United States Patent
Neyens et al.

(10) Patent No.: US 8,479,579 B2
(45) Date of Patent: Jul. 9, 2013

(54) MEASURING PROBES FOR MEASURING AND TAKING SAMPLES WITH A METAL MELT

(75) Inventors: Guido Jacobus Neyens, Opoeteren (BE); Dries Beyens, Kinrooi (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 251 days.

(21) Appl. No.: 13/104,050

(22) Filed: May 10, 2011

(65) Prior Publication Data
US 2011/0308319 A1 Dec. 22, 2011

(30) Foreign Application Priority Data

Jun. 18, 2010 (DE) .................. 10 2010 024 282

(51) Int. Cl.
*G01L 7/00* (2006.01)
*G01D 21/00* (2006.01)

(52) U.S. Cl.
USPC .......................................... 73/700; 73/866.5

(58) Field of Classification Search
None
See application file for complete search history.

(56) References Cited

U.S. PATENT DOCUMENTS

| | | | |
|---|---|---|---|
| 3,755,126 A * | 8/1973 | Misener et al. ............... 204/423 |
| 4,007,641 A | 2/1977 | Kelsey | |
| 4,105,507 A * | 8/1978 | VonKrusenstierna et al. .................. 205/783.5 |
| 4,503,716 A | 3/1985 | Wuensch | |
| 4,893,516 A * | 1/1990 | Knevels ........................ 73/866.5 |
| 5,332,449 A * | 7/1994 | Verstreken et al. ........... 136/234 |
| 5,421,215 A | 6/1995 | Cure et al. | |
| 5,883,387 A * | 3/1999 | Matsuyama et al. ............ 850/59 |
| 5,989,408 A * | 11/1999 | Baerts et al. ................ 205/783.5 |
| 6,051,833 A * | 4/2000 | Yasutake ........................... 850/3 |
| 6,142,664 A * | 11/2000 | Ikawa et al. .................... 374/140 |
| 6,156,174 A * | 12/2000 | Baerts et al. .................... 204/423 |
| 6,433,862 B1 * | 8/2002 | Schock et al. ................... 356/36 |
| 6,581,482 B2 * | 6/2003 | Cappa et al. ............... 73/864.55 |
| 6,811,742 B2 | 11/2004 | Knevels | |
| 7,370,544 B2 * | 5/2008 | Neyens et al. .............. 73/864.59 |
| 7,578,913 B2 * | 8/2009 | Merkens et al. ............... 204/421 |

(Continued)

FOREIGN PATENT DOCUMENTS

| DE | 2845566 A1 | 4/1979 |
|---|---|---|
| DE | 3000201 A1 | 7/1981 |

(Continued)

OTHER PUBLICATIONS

Search Report issued Apr. 4, 2012 in EP Application No. 11001762.1.

(Continued)

*Primary Examiner* — Freddie Kirkland, III
*Assistant Examiner* — Jermaine Jenkins
(74) *Attorney, Agent, or Firm* — Panitch Schwarze Belisario & Nadel LLP

(57) ABSTRACT

A measuring probe is provided for measuring and taking samples in a metal melt. The probe has a measuring head arranged on a lance, wherein the measuring head carries at least a temperature sensor and a sampling chamber, and wherein the sampling chamber is surrounded, at least partially, by the measuring head and includes an intake duct that extends through the measuring head. The intake duct includes an inner section, which extends in the measuring head and has a length L and a minimum diameter D at least at one site in the inner section. The ratio $L/D^2$ is less than 0.6 $mm^{-1}$.

20 Claims, 5 Drawing Sheets

U.S. PATENT DOCUMENTS

| | | | |
|---|---|---|---|
| 7,587,815 B2 * | 9/2009 | Yoshikawa et al. | 29/830 |
| 7,832,294 B2 * | 11/2010 | Neyens | 73/866.5 |
| 2005/0132823 A1 | 6/2005 | Knevels et al. | |
| 2007/0137286 A1 | 6/2007 | Neyens | |
| 2007/0137324 A1 | 6/2007 | Neyens | |

FOREIGN PATENT DOCUMENTS

| | | |
|---|---|---|
| DE | 3203505 A1 | 8/1983 |
| DE | 4204952 A1 | 8/1993 |
| DE | 19752743 C2 | 5/2000 |
| DE | 10148112 B4 | 1/2004 |
| DE | 10360625 B3 | 1/2005 |
| DE | 102005060493 B3 | 11/2006 |
| DE | 102005060492 B3 | 5/2007 |
| JP | 07306196 A | 11/1995 |

OTHER PUBLICATIONS

Office Action issued Jan. 18, 2012 in DE Application No. 10 2010 024 282.9.

Search Report issued Oct. 4, 2011 in BE Application No. 201100347.

* cited by examiner

MEASURING PROBES FOR MEASURING AND TAKING SAMPLES WITH A METAL MELT

BACKGROUND OF THE INVENTION

The invention relates to measuring probes for measuring and taking samples with a metal melt, the probe having a measuring head arranged on a lance, wherein the measuring head carries at least a temperature sensor and a sampling chamber, and wherein the sampling chamber is surrounded by the measuring head and includes an intake duct made of a quartz glass tube that extends through the measuring head.

Measuring probes of this type are known in principle and are used, among other uses, in steel-making in so-called converters or in electric arc furnaces.

In a converter (so-called BOF converter—technical term for basic oxygen furnace), a lance is used to blow oxygen into the metal melt. The converter is lined with refractory material, which withstands the erosion due to slag and heat during the oxygen blowing process in an optimal manner. Scrap metal and limestone (calcium oxide) are added into the converter in order to cool the melt and remove phosphorus, silicon, and manganese. The oxygen combusts the carbon to form carbon monoxide and carbon dioxide. Manganese, silicon, and phosphorus are oxidized and converted in the presence of calcium oxide and iron oxide to form slag.

Since the oxidation reaction is highly exothermic, the process needs to be cooled in order to control the temperature of the melt. Cooling is effected by adding scrap metal and iron ore during the blowing process. The oxygen blowing process itself takes approx. 15-20 minutes to complete, independent of the size of the converter, which can be approximately 70-400 tons. In this context, the oxygen flow rate of the lance is adapted to the size of the converter and/or the weight of the melt. Loading and unloading steel and slag including measuring the temperature and taking samples for analysis of the melt leads to a time period of 40-60 minutes between 2 tapping stages.

The overall process is characterized by its high productivity and leads to a steel with a low content of contaminations. In the tapping stage, the furnace is tilted and the product poured through a tapping hole into a casting ladle. During this operation, iron alloys are added into the casting ladle to control the steel composition. One important development of the oxygen blowing lance technique is to add inert gas, usually argon, through the converter floor to the melt, in order to stir the melt and the slag. This process increases the efficiency considerably, and both the iron loss and the phosphorus content decrease. Moreover, the heat and mass equilibrium of the process is improved, which reduces the costs.

Measuring probes for use in the converter are described, for example, in German Patents DE 10 2005 060 492 B3 and DE 10 2005 060 493 B3.

In an electric arc furnace, scrap metal is melted by the energy of an electric arc, which is generated between the tips of graphite electrodes and the conductive scrap metal load. For loading the scrap metal in the furnace, the three electrodes and the roof of the furnace are lifted up to expose a filler hole. The electrodes maintain the electric arc in accordance with the pre-selected voltage and pre-selected current, thus providing the energy required for melting and oxidizing. Electric arc furnaces have an internal diameter of approx. 6-9 meters and a capacity of 100-200 tons of steel. The time between two tapping stages in the furnaces is usually approx. 90-110 minutes.

Measuring probes for use in electric arc furnaces are known, for example, from German Patents DE 28 45 566 C2 and DE 103 60 625 B3, and German published patent application DE 32 03 505 A1.

For monitoring the processes in the converter or electric arc furnace, it is necessary to completely fill the sampling chamber of a measuring probe at relatively low temperatures in the process of taking a sample, whereby gas bubbles in the sample should be prevented. This type of taking a sample is not always easy, in particular during the blowing process in the converter, since the theoretical density of the steel melt varies strongly, on the one hand, due to the oxygen blowing process from above and, on the other hand, due to inert gas being blown in through the converter floor. Moreover, the industry tends to use furnaces that permit only little overheating of the melt (that is to say, only a small difference between the bath temperature and the liquidus temperature).

BRIEF SUMMARY OF THE INVENTION

Accordingly, the invention is based on the object of improving the existing measuring probes and samplers and facilitating largely gas-free sampling, i.e. to improve the sample quality. Preferably, the removal of the sample from the measuring probe should be simplified as well.

The object is achieved according to one embodiment of the invention in a measuring probe for measuring and taking samples in a metal melt, the probe having a measuring head arranged on a lance, wherein the measuring head carries at least a temperature sensor and a sampling chamber, wherein the sampling chamber is surrounded, at least partially, by the measuring head and includes an intake duct that extends through the measuring head and is preferably made of a quartz glass tube. In this embodiment the probe will allow for excellent, gas bubble-free samples if the ratio of the length L of a section of the quartz glass tube, which extends in the measuring head, and the square of a minimum diameter D of the quartz glass tube at least at one site in the inner section is $L/D^2 < 0.6$ mm$^{-1}$.

This ratio is preferably $<0.45$ mm$^{-1}$, and particularly preferably is $<0.3$ mm$^{-1}$. At low over-heating of the metal melt, a low ratio has proven to be advantageous, for example a ratio of $L/D^2 < 0.6$ mm$^{-1}$ at an over-heating of $>100°$ C. and a ratio of $L/D^2 < 0.3$ mm$^{-1}$ at an over-heating of $<80°$ C.

The object is also achieved in another embodiment of the invention in a measuring probe for measuring and taking samples in a metal melt, the probe having a measuring head arranged on a lance, wherein the measuring head carries at least a temperature sensor and a sampling chamber, and wherein the sampling chamber is surrounded, at least partially, by the measuring head and includes an intake duct that extends through the measuring head and is preferably made of a quartz glass tube. According to this embodiment, the measuring head has a counter-pressure $P_g < 20$ mbar.

The counter-pressure $P_g$ is determined, first by guiding a reference gas flux through a tube with two open ends and measuring pressure $P_1$ inside the tube, then inserting one end of the tube into the intake duct of the measuring head, guiding the same reference gas flux through the tube and measuring pressure $P_2$ inside the tube, and determining the counter-pressure $P_g$ of the measuring head from the difference $P_2 - P_1$. In this context, it is advantageous for the counter-pressure $P_g$ of the measuring head to be $<15$ mbar. Measuring heads of this type also ensure samples of high quality to be obtained.

It is advantageous, in particular, if the ratio of $L/D^2$ is less than $0.6$ mm$^{-1}$, preferably less than $0.45$ mm$^{-1}$, and wherein the counter-pressure $P_g$ of the measuring head in either case is less than 20 mbar.

It is expedient for the measuring head to be formed from a material selected from the group of ceramic materials, cement, steel, and foundry sand. Moreover, it is advantageous, in particular, for the sampling chamber to be surrounded, at least in part, by a sand body made of foundry sand. Moreover, the measuring head can be designed such that the lengths of the sampling chamber both in a first and a second direction, arranged to be perpendicular to each other, are larger than the length in a third direction, arranged to be perpendicular to the first and the second directions, and such that the intake duct opens into the sampling chamber perpendicular to the third direction. This corresponds to the design of so-called flat sampling chambers, which have a circular or oval or elongate cross-section and, arranged perpendicular to the cross-section, a smaller cross-section provided to be essentially rectangular, whereby the smaller cross-section can have rounded corners. Accordingly, the intake duct extends parallel to the larger and perpendicular to the smaller cross-section.

Moreover, it is advantageous for the measuring head to simultaneously carry at least an electrochemical sensor in order to enable more flexible and versatile utilization and simultaneously be able to measure more parameters of the metal melt.

It is advantageous to provide for the feasibility of venting the sampling chamber. The sampling chamber advantageously comprises two semi-spheres, which can be separated parallel to the longitudinal axis of the sampling chamber in known fashion and are held together by their edges in such a manner as to allow air to escape from the sampling chamber when liquid metal flows in, while the liquid metal cannot exit between the semi-spheres. It is advantageous for the sampling chamber to be arranged in a porous sand body in order to provide for venting. The two semi-spheres are pressed together by a clamp and the sampling chamber is fixed sufficiently in the sand body, such that the two semi-spheres do not open up in response to the ferrostatic pressure generated upon immersion into the melt. The edges of the semi-spheres can be provided, for example, with small holes or furrows to enable venting of the sampling chamber, whereby the formation of burs of melt exiting from the sampling chamber is prevented.

Customarily, the measuring probes according to the invention are immersed from above into the vessel containing the metal melt. The immersion process often proceeds automatically, for example with an automatic immersion lance. After the measurement is taken, the immersion lance bearing the measuring probe is pivoted sideways out of the vessel containing the metal melt and dropped. In the process, the measuring probe drops down several meters. After impact on the ground, the sample is undamaged and can easily be removed from the sampling chamber.

According to embodiments of the invention, the measuring probes described are used for measuring and taking samples in a metal melt arranged in a converter for steel melting during a blowing process, or for measuring and taking samples in a metal melt arranged in an electric arc furnace.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
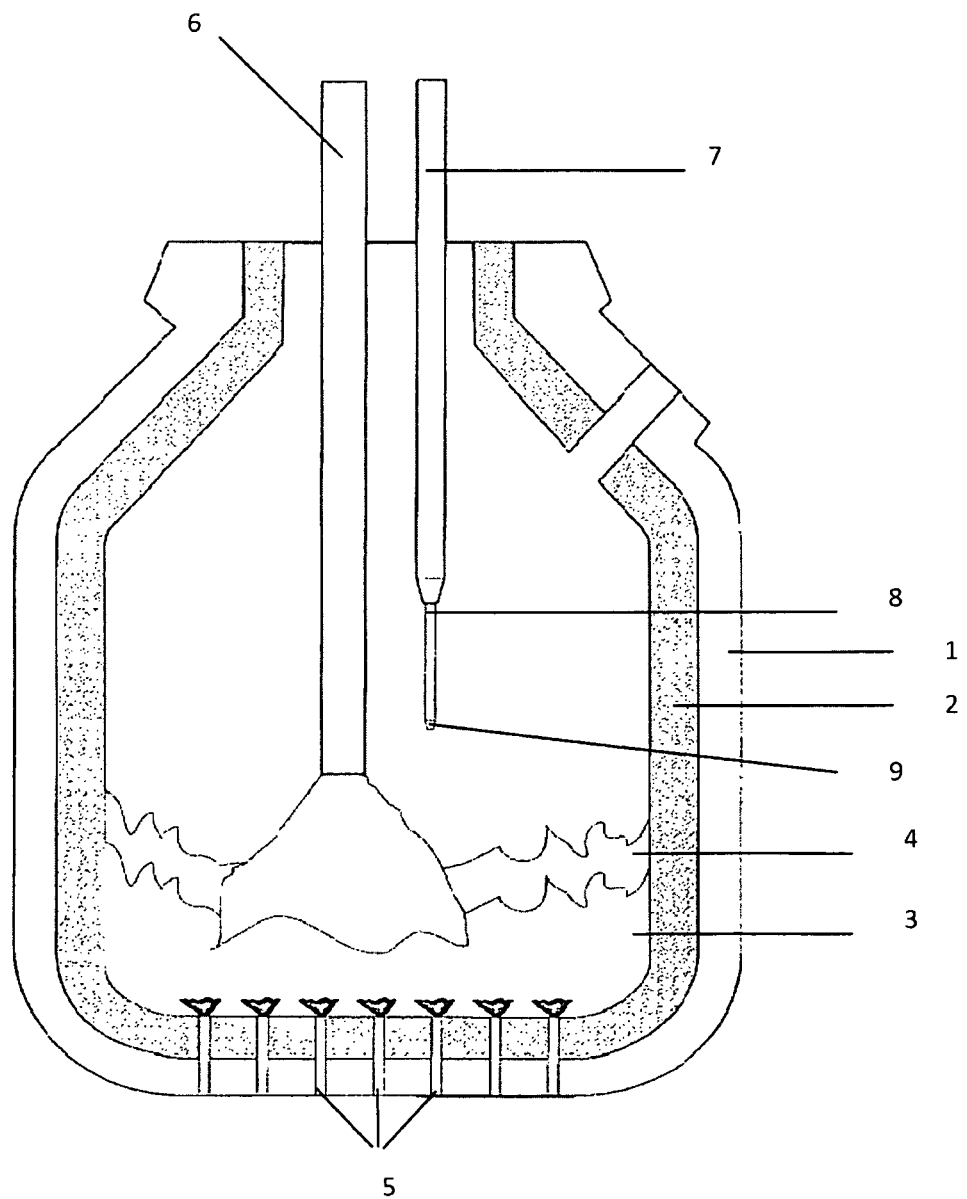
FIG. 1 is a schematic view of a cross-section through a converter.

FIG. 1 shows a converter 1 having a lining 2. The converter 1 contains a steel melt 3 on which a slag layer 4 is situated. For steel-making, argon is blown through the floor of the converter 1 through floor nozzles 5 into the metal melt. Oxygen is blown in from above by a blowing lance 6. Aside from the blowing lance 6, a so-called immersion lance 7, which has a measuring probe 8 having a measuring head 9 arranged on its immersion end, is introduced into the converter 1. The measuring process proceeds while oxygen is being blown in, usually approximately 2 minutes before the end of the oxygen blowing process. This involves measuring the temperature and taking a sample for determination of the carbon content. The results of the measurements allow the blowing model to be corrected in order to be able to alter the quality of the steel melt.

A second measurement may be performed after completion of the oxygen blowing process. This usually involves measuring the temperature and the active oxygen content in the steel melt and taking a sample for analysis in the laboratory for determination of the final composition of the steel. Based on the oxygen content, the current carbon content in the steel can be determined within a few seconds. Moreover, the requisite quantity of a deoxidation agent (aluminum) can be calculated.

Figure 2:
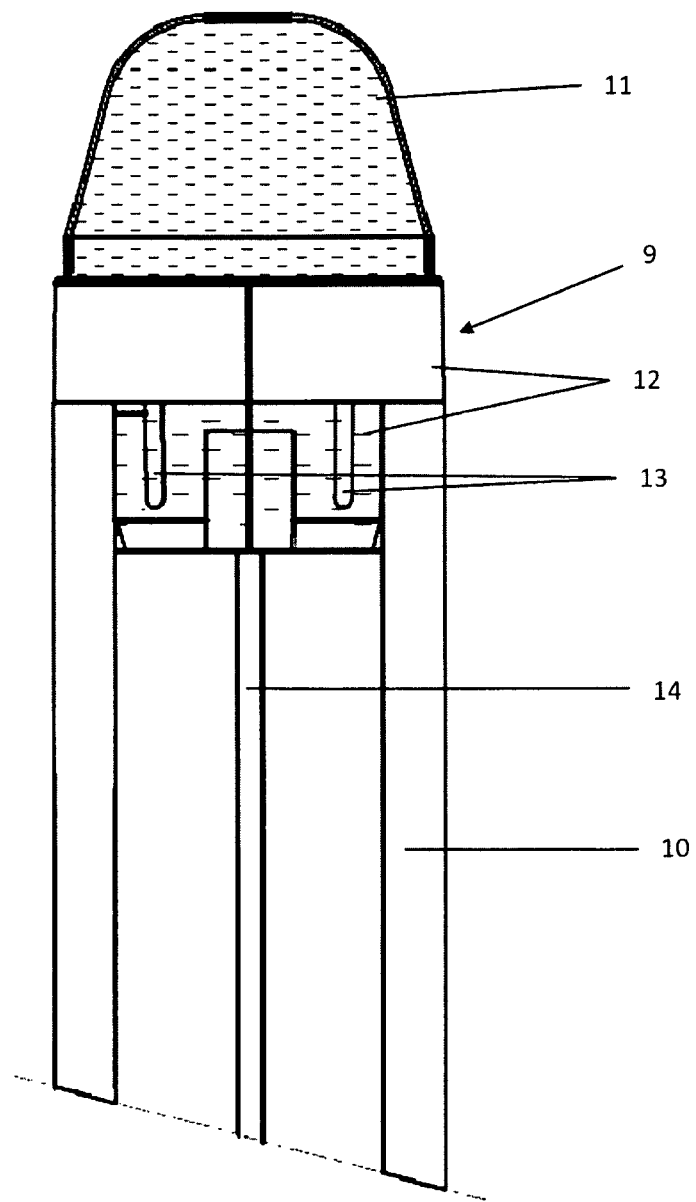
FIG. 2 is a schematic view of a measuring probe according to an embodiment of the invention having a measuring head.

The measuring probe shown in FIG. 2 has the measuring head 9 arranged on the immersion end of a carrier tube 10. For protection of the intake orifice and sensors, the measuring head 9 includes a plastic cap 11, which combusts during passage through the slag 4, thus releasing the sensor system and intake orifice into the metal melt. The plastic cap 11 can be supplemented on its inside by a metal cap or metal layer, which can be formed from steel and dissolves in the steel melt in which the measuring probe is used. The measuring head 9 includes a sand body 12 made of foundry sand, which includes ribs 13 by which the sand body 12 is pressed into the carrier tube 10 in order to ensure a firm hold. Connection cables 14 are arranged on the rear-side end of the measuring head 9 and are used to transmit the signals obtained by the sensors through the carrier tube 10 and the immersion lance 7 to an analytical facility.

Figure 3:
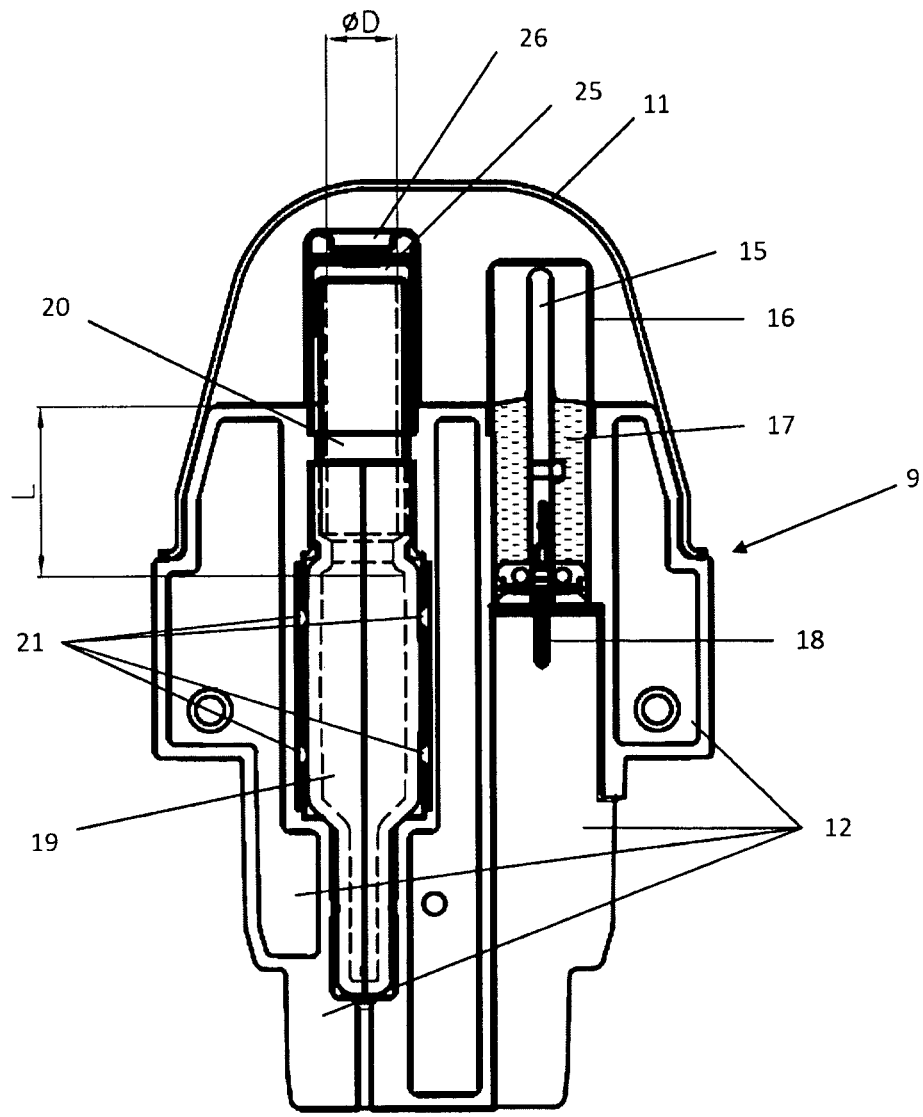
FIG. 3 is a section through the measuring head according to an embodiment of the invention.

The measuring head 9, shown schematically in a cross-section in FIG. 3, shows a thermocouple as temperature sensor 15, which is surrounded by a metal cap 16 and is arranged in the measuring head 9 by a refractory cement 17. On its rear end situated on the inside of the measuring head 9, the temperature sensor includes a connecting element 18 for connection of the thermocouple wires to the connection cable. Moreover, a sampler having a sampling chamber 19 and a quartz glass tube 20 as intake tube are also arranged in the sand body 12, which is made of foundry sand, of the measuring head 9. The sampling chamber 19 is fixed in the sand body 12 by sand ribs 21 of the sand body 12 by press-fitting.

The quartz glass tube projects by approx. 1 cm from the sand body. The external intake orifice of the quartz glass tube 20 is closed by a metal cap 25 (made of steel) and, arranged above it, a cardboard cap 26, which are destroyed upon or after immersion into the steel melt and release the external intake orifice of the quartz glass tube. The length L denotes the length of the intake tube arranged in the sand body 12 of the measuring head 9 between its entry into the sampling chamber 19 and its exit from the sand body 12. This is the so-called installed length. The diameter D denotes the minimum diameter within the installed length L. In the example shown, the ratio $L/D^2=0.22$ $mm^{-1}$ and leads to a bubble-free sample, whereas the ratio is approximately 1.43 $mm^{-1}$ in the case of corresponding probes according to the prior art.

Figure 4:
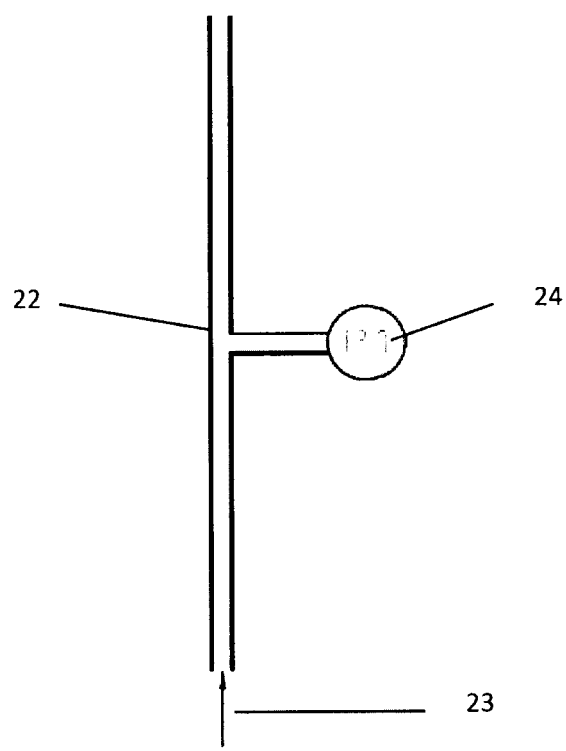
FIG. 4 is a schematic view illustrating the pressure measurement on the open tube.

The pressure measurement proceeds initially according to the schematic diagram shown in FIG. 4 in a tube 22, which is open on both ends and has an external diameter suitably adapted to allow it to be slid into the quartz glass tube 20. The arrow 23 indicates the flow direction of the flowing gas, preferably air, the pressure $P_1$ of which is determined by the pressure gauge 24. The length of the tube 22 between the pressure gauge 24 and the quartz glass tube 20 is approximately 2 cm, the internal diameter is approximately 4 mm.

Figure 5:
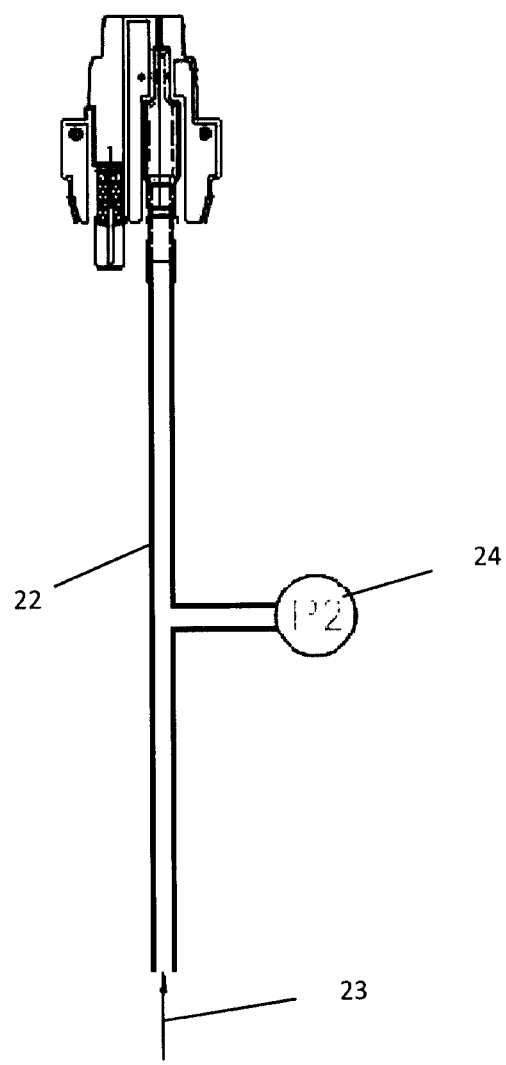
FIG. 5 is a schematic view illustrating the pressure measurement on the measuring head.

FIG. 5 shows a schematic view of the tube 22 slid into the quartz glass tube 20 of the sampler after the measurement according to FIG. 4. With gas being introduced again, pressure $P_2$ is measured by the pressure gauge. The difference $P_2-P_1$ is the counter-pressure $P_g$ of the measuring head. The pressure is measured in each case while a gas flows through at a flow rate of 800 l/hr, whereby the gas flow is based on a so-called "standard liter," i.e. measured at room temperature of 20° C. and a standard air pressure of 1013 hPa. The counter-pressure determined in the example shown is less than 15 mbar. Samples of good quality are obtained with an arrangement with this counter-pressure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A measuring probe for measuring and taking samples in a metal melt, the probe comprising a measuring head arranged on a lance, the measuring head carrying at least a temperature sensor and a sampling chamber, wherein the sampling chamber is at least partially surrounded by the measuring head and includes an intake duct extending through the measuring head, the intake duct including an inner section extending in the measuring head and having a length L and a minimum diameter D at least at one site in the inner section, and wherein the ratio $L/D^2$ is less than 0.6 $mm^{-1}$.

2. The measuring probe according to claim 1, wherein the ratio $L/D^2$ is less than 0.45 $mm^{-1}$.

3. The measuring probe according to claim 2, wherein the ratio $L/D^2$ is less than 0.3 $mm^{-1}$.

4. The measuring probe according to claim 1, wherein the measuring head comprises a material selected from the group of ceramics, cement, steel, and foundry sand.

5. The measuring probe according to claim 1, wherein the intake duct comprises a quartz glass tube.

6. The measuring probe according to claim 1, wherein the sampling chamber is at least partially surrounded by a sand body comprising foundry sand.

7. The measuring probe according to claim 1, wherein lengths of the sampling chamber in each of a first direction and a second direction are arranged to be perpendicular to each other and are larger than a length in a third direction arranged perpendicular to the first direction and the second direction, and wherein the intake duct opens into the sampling chamber perpendicular to the third direction.

8. The measuring probe according to claim 1, wherein the measuring head carries in addition at least one electrochemical sensor.

9. A method for measuring and taking samples during a blowing process in a metal melt arranged in a converter for steel-making, the method comprising using the measuring probe according to claim 1.

10. A method for measuring and taking samples in a metal melt arranged in an electric arc furnace, the method comprising using the measuring probe according to claim 1.

11. A measuring probe for measuring and taking samples in a metal melt, the probe comprising a measuring head arranged on a lance, the measuring head carrying at least a temperature sensor and a sampling chamber, wherein the sampling chamber is at least partially surrounded by the measuring head and includes an intake duct extending through the measuring head, and wherein the measuring head has a counter-pressure $P_g$ of less than 20 mbar, the counter-pressure being determined by first guiding a reference gas flux through a tube having two open ends and measuring a pressure $P_1$ inside the tube, then inserting one end of the tube into the intake duct of the measuring head, guiding the same reference gas flux through the tube and measuring a pressure $P_2$ inside the tube, and determining the counter-pressure $P_g$ of the measuring head from the difference $P_2-P_1$.

12. The measuring probe according to claim 11, wherein the counter-pressure $P_g$ of the measuring head is less than 15 mbar.

13. The measuring probe according to claim 11, wherein the intake duct includes an inner section extending in the measuring head and having a length L and a minimum diameter D at least at one site in the inner section, and wherein the ratio $L/D^2$ is less than 0.6 $mm^{-1}$.

14. The measuring probe according to claim 13, wherein the ratio $L/D^2$ is less than 0.45 $mm^{-1}$.

15. The measuring probe according to claim 13, wherein the ratio $L/D^2$ is less than 0.3 $mm^{-1}$.

16. The measuring probe according to claim 11, wherein the measuring head comprises a material selected from the group of ceramics, cement, steel, and foundry sand.

17. The measuring probe according to claim 11, wherein the intake duct comprises a quartz glass tube.

18. The measuring probe according to claim 11, wherein the sampling chamber is at least partially surrounded by a sand body comprising foundry sand.

19. The measuring probe according to claim 11, wherein lengths of the sampling chamber in each of a first direction and a second direction are arranged to be perpendicular to each other and are larger than a length in a third direction arranged perpendicular to the first direction and the second direction, and wherein the intake duct opens into the sampling chamber perpendicular to the third direction.

20. The measuring probe according to claim 11, wherein the measuring head carries in addition at least one electrochemical sensor.

* * * * *